US012127823B2

(12) United States Patent
Kim et al.

(10) Patent No.: US 12,127,823 B2
(45) Date of Patent: *Oct. 29, 2024

(54) PULSE MEASUREMENT APPARATUS, A METHOD THEREFOR, AND A VEHICLE SYSTEM THEREFOR (71) Applicants: HYUNDAI MOTOR COMPANY, Seoul (KR); KIA CORPORATION, Seoul (KR); NIDEC MOBILITY KOREA CORPORATION, Anseong-si (KR)

(72) Inventors: Eung Hwan Kim, Seoul (KR); Seul Ki Jeon, Suwon-si (KR); Nam Woong Hur, Hwaseong-si (KR); Gyun Ha Kim, Incheon (KR); Sang Won Lee, Gwangmyeong-si (KR); Ho Jin Lee, Bucheon-si (KR); Sang Bum Kim, Dongducheon-si (KR)

(73) Assignees: KIA CORPORATION, Seoul (KR); HYUNDAI MOTOR COMPANY, Seoul (KR); NIDEC MOBILITY KOREA CORPORATION, Anseong-si (KR)

(*) Notice: Subject to any disclaimer, the term of this patent is extended or adjusted under 35 U.S.C. 154(b) by 583 days.

This patent is subject to a terminal disclaimer.

(21) Appl. No.: 17/369,536

(22) Filed: Jul. 7, 2021

(65) Prior Publication Data
US 2021/0330210 A1 Oct. 28, 2021

Related U.S. Application Data (62) Division of application No. 15/920,012, filed on Mar. 13, 2018, now Pat. No. 11,083,384.

(30) Foreign Application Priority Data

Dec. 4, 2017 (KR) .................. 10-2017-0164938

(51) Int. Cl.
A61B 5/024 (2006.01)
A61B 5/00 (2006.01)
A61B 5/0507 (2021.01)

(52) U.S. Cl.
CPC ........ *A61B 5/02444* (2013.01); *A61B 5/7225* (2013.01); *A61B 5/725* (2013.01); *A61B 5/0507* (2013.01); *A61B 5/6893* (2013.01)

(58) Field of Classification Search
None
See application file for complete search history.

(56) References Cited

U.S. PATENT DOCUMENTS 10,405,806 B2   9/2019   Baik et al.
10,624,586 B2   4/2020   Noguchi et al.
(Continued)

FOREIGN PATENT DOCUMENTS

CN   103400069 A   11/2013
CN   204926092 U   12/2015
(Continued)

OTHER PUBLICATIONS

Office Action cited in Chinese app No. 201810288208.6; Nov. 29, 2021; 19 pp.
(Continued)

*Primary Examiner* — Jay B Shah
(74) *Attorney, Agent, or Firm* — Lempia Summerfield Katz LLC (57) ABSTRACT A pulse measurement system of a vehicle includes at least one vehicle device and a pulse measurement apparatus. The vehicle device is configured to recognize a user who rides in the vehicle and to provide information of the user. The pulse measurement apparatus is configured to recognize the user based on the information of the user received from the at least one vehicle device, to set a frequency band of a filter (Continued)

to a first frequency band or a second frequency band based on information of the recognized user, and to detect pulse information of the user based on a signal extracted from the signal reflected from the user by the filter when measuring a pulse of the user.

12 Claims, 7 Drawing Sheets

(56) References Cited

U.S. PATENT DOCUMENTS

| | | |
|---|---|---|
| 2013/0245437 A1 | 9/2013 | Gamble |
| 2014/0309806 A1 | 10/2014 | Ricci |
| 2014/0309849 A1 | 10/2014 | Ricci |
| 2016/0256116 A1 | 9/2016 | Baik et al. |
| 2016/0302735 A1 | 10/2016 | Noguchi et al. |
| 2017/0143272 A1 | 5/2017 | Brouse |
| 2017/0216672 A1 | 8/2017 | Wisbey |
| 2017/0258405 A1 | 9/2017 | Sato |

FOREIGN PATENT DOCUMENTS

| | | |
|---|---|---|
| CN | 105873503 A | 8/2016 |
| CN | 107085709 A | 8/2017 |
| JP | 2009055997 A | 3/2009 |
| JP | 2011115459 A | 6/2011 |
| JP | 2017144132 A | 8/2017 |
| KR | 20160108081 A | 9/2016 |
| WO | 2004075746 A2 | 9/2004 |
| WO | 2016088564 A1 | 6/2016 |

OTHER PUBLICATIONS

Office Action cited in corresponding Korean patent application No. KR 10-2017-0164938; Jan. 3, 2022; 11 pp.
Notification of Allowance cited in Chinese app No. 201810288208.6; Apr. 19, 2022; 6 pp.

FIG. 7

PULSE MEASUREMENT APPARATUS, A METHOD THEREFOR, AND A VEHICLE SYSTEM THEREFOR

CROSS-REFERENCE TO RELATED APPLICATION

This application is a division of U.S. patent application Ser. No. 15/920,012 entitled "Pulse Measurement Apparatus, a Method Therefor, and a Vehicle System Therefor" and filed Mar. 13, 2018, and which claimed priority to and the benefit of Korean Patent Application No. 10-2017-0164938, filed on Dec. 4, 2017 in the Korean Intellectual Property Office. The entire contents of these prior filed applications are incorporated herein by reference.

TECHNICAL FIELD

The present disclosure relates to a pulse measurement apparatus, a method therefor, and a vehicle system therefor.

BACKGROUND

A vehicle may be equipped with electronic control devices for performing a corresponding operation depending on a biometric state of a user who rides in the vehicle. Electronic control devices may measure biometric information of the user such as pulse information using a contact or non-contact sensor.

If measuring biometric information in a non-contact manner, the electronic control devices may read a reflection signal for a radio wave signal transmitted to the user in a state where the user maintains an accurate position and may measure biometric information of the user. In this case, it takes a little time to read the biometric information of the user. If the user is moved, it takes more time to measure biometric information.

SUMMARY

The present disclosure has been made to solve the above-mentioned problems occurring in the prior art, while advantages achieved by the prior art remain intact.

An aspect of the present disclosure provides a pulse measurement apparatus for shortening a pulse measurement time by setting a filtering frequency band of a received signal using learning data for pulse information of a user when measuring a pulse of the user in a non-contact manner.

The technical problems to be solved by the present disclosure are not limited to the aforementioned problems. Other technical problems not mentioned herein will be clearly understood from the following description by those skilled in the art to which the present disclosure pertains.

According to an aspect of the present disclosure, a pulse measurement apparatus may include a communicator configured to transmit a first signal to a user and receive a second signal reflected from the user during a predetermined time, a filter configured to extract a signal of a set frequency band from the second signal, a setting device configured to set a frequency band of the filter to a first frequency band or a second frequency band, and a pulse detector configured to measure a pulse from the signal extracted by the filter, analyze an average pulse, and detect pulse information of the user from the analyzed result.

The apparatus may further include a user recognizing device configured to recognize the user based on information of the user who rides in a vehicle.

If the recognized user is not a previously registered user, the setting device may be configured to set the frequency band of the filter to the first frequency band. If the recognized user is the previously registered user, the setting device may be configured to set the frequency band of the filter to the second frequency band based on learning data stored in response to the user.

The apparatus may further include a learning device configured to learn the detected pulse information of the user and generate learning data based on the learned result.

The learning device may be configured to store the generated learning data in response to the user.

If there is learning data previously stored in response to the user, the learning device may be configured to learn the detected pulse information of the user and the stored learning data and may be configured to update the stored learning data based on the learned result.

The user recognizing device may be configured to recognize the user based on user information provided from a vehicle device.

The apparatus may further include a storage configured to register information of the user and store the detected pulse information of the user in response to the registered information of the user.

According to another aspect of the present disclosure, a pulse measurement method may include setting a frequency band of a filter to a first frequency band or a second frequency band, transmitting a first signal to a user and receiving a second signal reflected from the user during a predetermined time, extracting a signal of a frequency band set in the filter from the second signal, and measuring a pulse from the extracted signal, analyzing an average pulse, and detecting pulse information of the user from the analyzed result.

Before the setting, the method may further include recognizing the user based on information of the user who rides in a vehicle.

If the recognized user is not a previously registered user, the setting may include setting the frequency band of the filter to the first frequency band. If the recognized user is the previously registered user, the setting may include setting the frequency band of the filter to the second frequency band based on learning data stored in response to the user.

The method may further include learning the detected pulse information of the user, generating learning data based on the learned result, and storing the generated learning data in response to the user.

If there is learning data previously stored in response to the user, the method may further include learning the detected pulse information of the user and the stored learning data and updating the stored learning data based on the learned result.

The recognizing of the user may include recognizing the user based on user information provided from a vehicle device.

If the recognized user is not a previously stored user, the method may further include registering information of the recognized user and storing the detected pulse information of the user in response to the registered information of the user.

According to another aspect of the present disclosure, a vehicle system may include at least one vehicle device configured to recognize a user who rides in a vehicle and provide information of the user and a pulse measurement apparatus configured to recognize the user based on the information of the user, set a frequency band of a filter to a first frequency band or a second frequency band based on information of the recognized user, and detect pulse information of the user based on a signal extracted from the signal reflected from the user by the filter when measuring a pulse of the user. The information of the user may be received from the at least one vehicle device.

If the recognized user is not a previously registered user, the pulse measurement apparatus may be configured to set the frequency band of the filter to the first frequency band. If the recognized user is the previously registered user, the pulse measurement apparatus may be configured to set the frequency band of the filter to the second frequency band based on learning data stored in response to the user.

The pulse measurement apparatus may be configured to output the detected pulse information of the user to at least one of a control system or a display device in the vehicle.

The at least one vehicle device may include at least one of a smart key control device, a vehicle communication device, and a seat control device.

The pulse measurement apparatus may be configured to be installed in a seat of the vehicle and measure a pulse of a user who sits on the seat by a radio wave signal.

BRIEF DESCRIPTION OF THE DRAWINGS

The above and other objects, features, and advantages of the present disclosure will be more apparent from the following detailed description taken in conjunction with the accompanying drawings.

DETAILED DESCRIPTION

Hereinafter, embodiments of the present disclosure will be described in detail with reference to the accompanying drawings. Although the same elements may be displayed on different drawings, it should be noted that the same elements have the same denotations. If it is determined that a detailed description of related well-known configurations or functions blurs the gist of an embodiment of the present disclosure in describing an embodiment of the present disclosure, the detailed description has been omitted.

In describing elements of embodiments of the present disclosure, the terms $1^{st}$, $2^{nd}$, first, second, A, B, (a), (b), and the like may be used herein. These terms are only used to distinguish one element from another element and do not limit the corresponding elements irrespective of the nature, turn, or order of the corresponding elements. Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art and are not to be interpreted as having ideal or excessively formal meanings unless clearly defined as having such in the present application.

Figure 1:
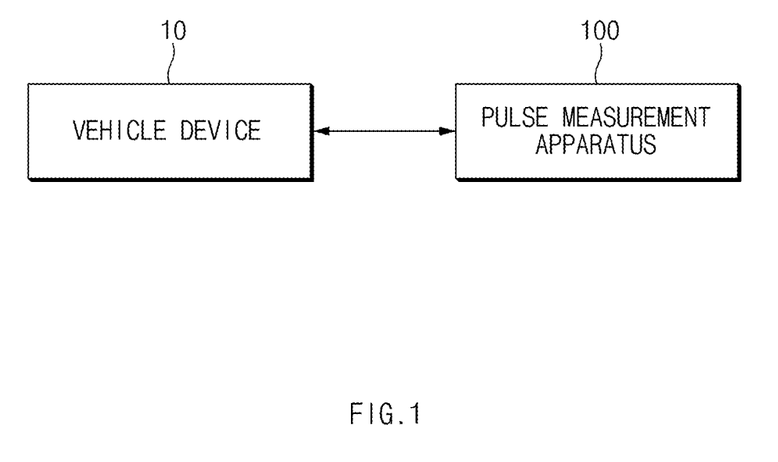
FIG. 1 is a block diagram illustrating a vehicle system to which a pulse measurement apparatus is applied, according to an embodiment of the present disclosure.

FIG. 1 is a block diagram illustrating a vehicle system to which a pulse measurement apparatus is applied according to an embodiment of the present disclosure.

Referring to FIG. 1, the vehicle system according to an embodiment of the present disclosure may include a vehicle device 10 and a pulse measurement apparatus 100.

The vehicle device 10 may be communicatively connected with the pulse measurement apparatus 100 and may provide information of a user to the pulse measurement apparatus 100.

The pulse measurement apparatus 100 may be a device that measures, in a non-contact manner, a pulse of the user who rides in a vehicle. As an example, the pulse measurement apparatus 100 may be installed in a seat in the vehicle and may measure a pulse of the user who sits on the seat.

The pulse measurement apparatus 100 may store pulse information of the user and may analyze the stored average pulse of the user, thereby learning pulse information of the user.

In this case, the pulse measurement apparatus 100 may adjust a frequency band of a signal for pulse measurement based on pulse information learned for the user and may measure a pulse of the user based on a signal received with the adjusted frequency band.

The pulse measurement apparatus 100 may receive user information from the vehicle device 10, which is communicatively connected with the pulse measurement apparatus 100 and may recognize the user from the received user information. If the recognized user is a previously registered user, the pulse measurement apparatus 100 may call learned pulse information of the recognized user.

If the recognized user is not the previously registered user based on user information received from the vehicle device 10, the pulse measurement apparatus 100 may measure a pulse of the user and may analyze an average pulse of the user. In this case, the pulse measurement apparatus 100 may register the received user information and may store pulse information corresponding to the registered user information.

A description will be given in detail of a detailed configuration of the pulse measurement apparatus 100 with reference to FIG. 2.

The pulse measurement apparatus 100 according to an embodiment of the present disclosure may be implemented in a vehicle. In this case, the pulse measurement apparatus 100 may be integrated with internal control units of the vehicle. Alternatively, the pulse measurement apparatus 100 may be implemented to be independent of the internal control units of the vehicle and may be connected with the internal control units by a separate connection means.

Figure 2:
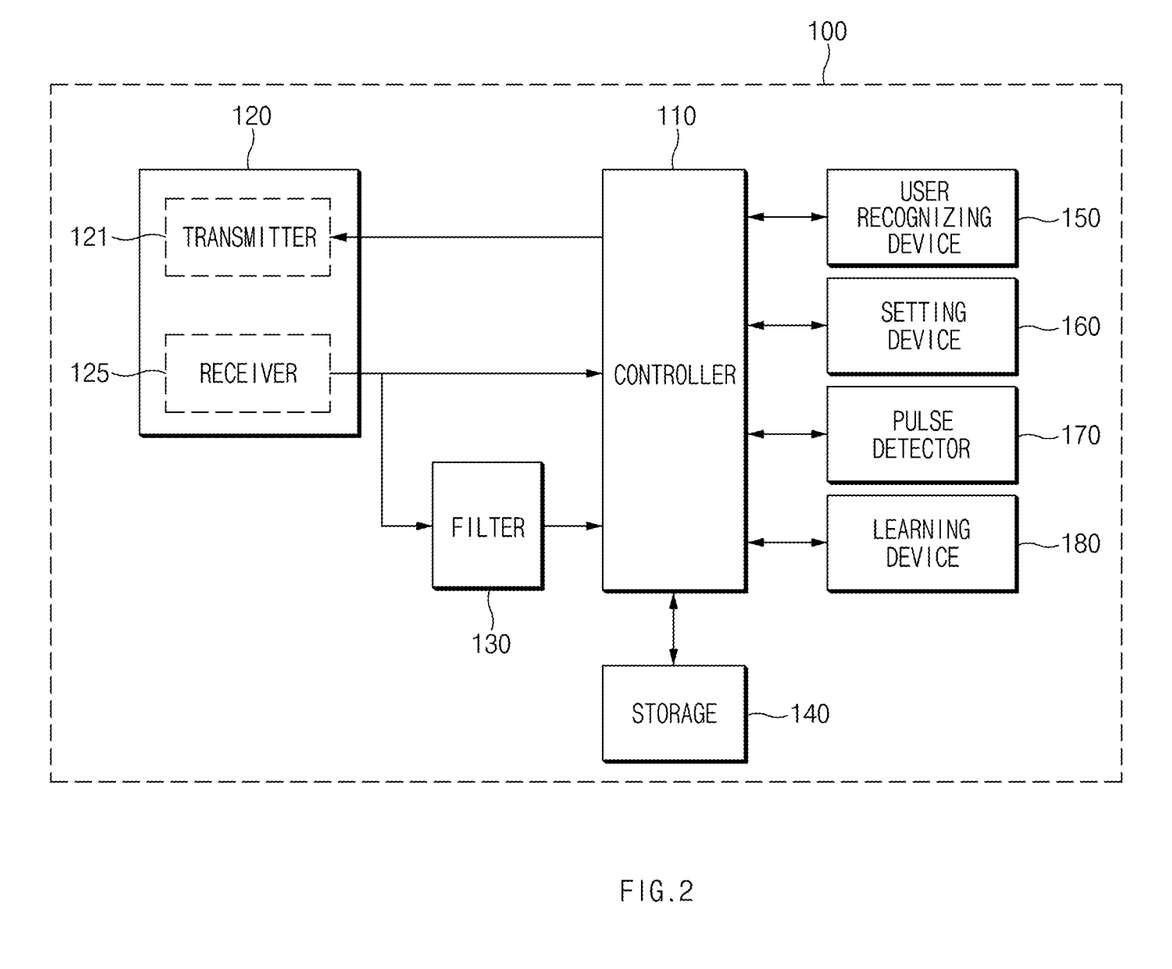
FIG. 2 is a block diagram illustrating a configuration of a pulse measurement apparatus according to an embodiment of the present disclosure.

FIG. 2 is a block diagram illustrating a configuration of a pulse measurement apparatus according to an embodiment of the present disclosure.

Referring to FIG. 2, a pulse measurement apparatus 100 may include a controller 110, a communicator 120, a filter 130, a storage 140, a user recognizing device 150, a setting device 160, a pulse detector 170, and a learning device 180. The controller 110, the setting device 160, the pulse detector 170, and the learning device 180 of the pulse measurement apparatus 100 according to an embodiment of the present disclosure may be implemented as one or more processors.

The controller 100 may process a signal transmitted between the elements of the pulse measurement apparatus 100.

The communicator 120 may include a communication module for supporting a communication interface with electronics and/or control units mounted on a vehicle. As an example, the communication module may be communicatively connected with at least one vehicle device 10 of FIG. 1 and may receive information of a user from the vehicle device 10. The communication module may include a module for supporting vehicle network communication such as controller area network (CAN) communication, local interconnect network (LIN) communication, and flex-ray communication. Further, the communication module may include a module for wireless Internet access or a module for short range communication. Wireless Internet technologies may include a wireless local area network (WLAN), wireless broadband (Wibro), wireless-fidelity (Wi-Fi), world interoperability for microwave access (Wimax), and the like. Short range communication technologies may include Bluetooth, ZigBee, ultra-wideband (UWB), radio frequency identification (RFID), infrared data association (IrDA), and the like.

The communicator 120 may transmit a radio wave signal to a user using a Doppler system and may receive a signal reflected from the user, thereby transmitting the received signal to the controller 110.

The communicator 120 may include a transmitter 121 for transmitting a first signal for pulse measurement to the user and a receiver 125 for receiving a second signal in which the first signal transmitted by the transmitter 121 is reflected from the user. As an example, the first signal may be a radio wave signal of a 24 GHz band. The second signal may include a signal of a plurality of bands.

The filter 130 may extract a signal corresponding to a predetermined frequency band from the second signal received by the receiver 125 and may block a signal of another band. As an example, the filter 130 may extract a signal of a predetermined reference band (hereinafter referred to as "first frequency band") from the second signal received via the receiver 125 and may block a signal of the other frequency band. The signal extracted by the filter 130 may be transmitted to the controller 110.

A predetermined frequency band set in the filter 130 may be adjusted by the setting device 160. In this case, the filter 130 may extract a signal of a frequency band (hereinafter referred to as "second frequency band") adjusted by the setting device 160 from the second signal received via the receiver 125 and may transmit the extracted signal to the controller 110.

The filter 130 may be implemented in the form of a hardware module. According to an embodiment, the filter 130 may be implemented in the form of a software module.

The storage 140 may store data, an algorithm, and/or the like necessary for operating the pulse measurement apparatus 100.

The storage 140 may store information of a first frequency band of the filter 130 and may store information of a second frequency band adjusted by the setting device 160. Further, the storage 140 may store registered user information and may store pulse information stored in response to the user information and/or learning data of the pulse information.

The storage 140 may store an instruction and/or an algorithm for detecting a pulse of the user based on a received signal and for analyzing an average pulse of the user from the detected pulse information. The storage 140 may store a learning algorithm for learning pulse information of the user.

The storage 140 may include storage media, such as a random-access memory (RAM), a static RAM (SRAM), a read-only memory (ROM), a programmable ROM (PROM), and an electrically erasable PROM (EEPROM).

If a pulse measurement event occurs, the user recognizing device 150 may recognize the user. The user recognizing device 150 may recognize the user based on information input from the user. The user recognizing device 150 may receive user information from the vehicle device 10 connected via the communicator 120. The user recognizing device 150 may recognize the user based on the user information received from the vehicle device 10.

The user recognizing device 150 may determine whether the recognized user is a previously registered user. If determining that the recognized user is the previously registered user, the user recognizing device 150 may transmit information about the recognized user and registration information of the user to the setting device 160 and/or the controller 110.

If determining that the recognized user is not the previously registered user, the user recognizing device 150 may transmit the information about the recognized user to the setting device 160 and/or the controller 110. The user recognizing device 150 may register information about the recognized user in the storage 140 depending on a request of the user.

The setting device 160 may set a frequency band of a signal passing through the filter 130. If the user recognized by the user recognizing device 150 is a user that is not registered, the setting device 160 may set a frequency band of the filter 130 to a predefined first frequency band. Although there is no pulse information learned in response to the user recognized by the user recognizing device 150, the setting device 160 may set the frequency band of the filter 130 to the predefined first frequency band.

If the user recognized by the user recognizing device 150 is the previously registered user and if there is pulse information learned in response to the user, the setting device 160 may adjust a frequency band of the filter 130 based on the pulse information learned in response to the user.

If a frequency band of the filter 130 is set to the first frequency band or a second frequency band by the setting device 160 when a pulse measurement event occurs, the controller 110 may control the transmitter 121 to transmit a first signal during a predetermined time through the transmitter 121. If a signal of the first frequency band or the second frequency band extracted by the filter 130 from a second signal received in response to the first signal transmitted during the predetermined time is received, the controller 110 may store the received signal in the storage 140 and may transmit the stored signal to the pulse detector 170.

The pulse detector 170 may measure a pulse from signals of the first frequency band or the second frequency band extracted by the filter 130 and may analyze an average pulse, thereby detecting pulse information of the user. The pulse detector 170 may store the detected pulse information of the user in the storage 140 and may output the stored information.

If the frequency band of the filter 130 is set to the first frequency band, the pulse detector 170 may analyze signals of the first frequency band extracted by the filter 130 to measure a pulse and may analyze an average pulse to detect pulse information of the user.

If the frequency band of the filter 130 is set to the second frequency band that is determined based on learning data for previous pulse information detected from the user, the pulse detector 170 may analyze signals of the second frequency band extracted by the filter 130 to measure a pulse and may analyze an average pulse to detect pulse information of the user. The second frequency band may be determined from learning data for previous pulse information detected from the user.

The pulse detector 170 may output pulse information of the user to a control system in a vehicle, connected via the communicator 120. The control system in the vehicle may be a system that performs a corresponding operation based on biometric information of the user. Further, the pulse detector 170 may output the pulse information of the user to a display device in the vehicle, connected via the communicator 120.

The learning device 180 may learn pulse information of the user, detected based on signals of the first frequency band or the second frequency band, and may generate learning data based on the learning result. In this case, the generated learning data may be stored in response to information of the user, registered in the storage unit 140.

If there is no learning data previously stored in response to the user, the learning device 180 may learn pulse information of the user, detected by signals of the first frequency band, and may generate learning data based on the learning result. If there is learning data previously stored in response to the user, the learning device 180 may learn pulse information of the user, detected based on signals of the second frequency band, and the previously stored learning data. The learning device 180 may update learning data stored in the storage 140 based on the learning result. The learning data stored in response to the user may be updated whenever a pulse is measured from the user.

The learning device 180 may learn pulse information of the user by a learning algorithm installed in the pulse measurement apparatus 100. The learning device 180 may receive a learning result for pulse information of the user from an external learning server connected via the communicator 120 and may generate learning data for pulse information of the user based on the received learning result.

The pulse measurement device 100 according to an embodiment of the present disclosure, which performs the above-mentioned operation, may be implemented in the form of an independent hardware device including a memory and a processor for processing each operation or may be driven in the form of being included in another hardware device such as a microprocessor or a universal computer system.

Figure 3:
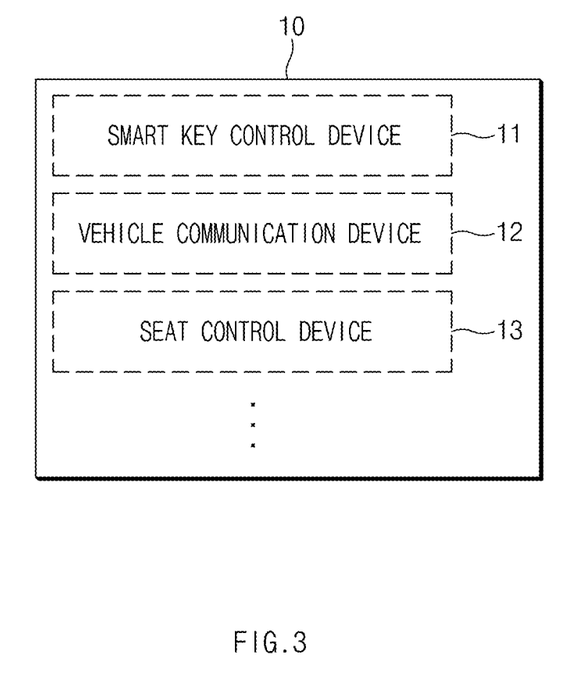
FIG. 3 is a block diagram illustrating a configuration of a vehicle device according to an embodiment of the present disclosure.

FIG. 3 is a block diagram illustrating a configuration of a vehicle device 10 according to an embodiment of the present disclosure.

The vehicle device 10 may be communicatively connected with a pulse measurement apparatus 100 of FIG. 1 and may provide information of a user to the pulse measurement apparatus 100. The vehicle device 10 may transmit and receive a signal with the pulse measurement apparatus 100 in a vehicle network communication mode, a wireless Internet communication mode, and/or a short-range communication mode.

Referring to FIG. 3, the vehicle device 10 may include a smart key control device 11 for providing a key identifier (ID) of a smart key to the pulse measurement apparatus 100. The vehicle device 10 may also include a vehicle communication device 12, which is communicatively connected with a user terminal in a wireless communication mode in a vehicle, for providing information registered in the user terminal to the pulse measurement apparatus 100. The vehicle device 10 may also include a seat control device 13 for providing information of the user that is registered in a memory seat system, such as an integrated memory system (IMS), to the pulse measurement apparatus 100, and/or the like. The vehicle device 10 may correspond to any device for providing information of the user other than the above-mentioned devices.

Figure 4A:
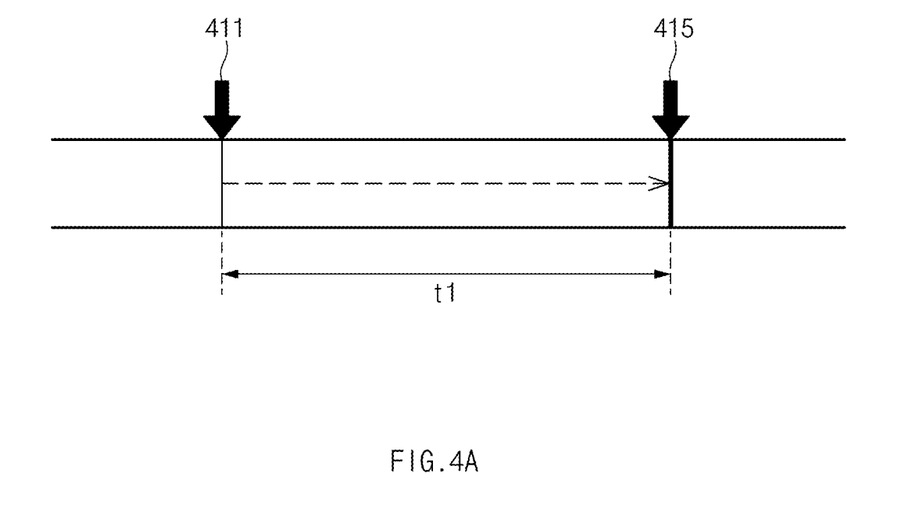
FIGS. 4A and 4B are drawings illustrating an operation of a pulse measurement apparatus according to an embodiment of the present disclosure.
Figure 4B:
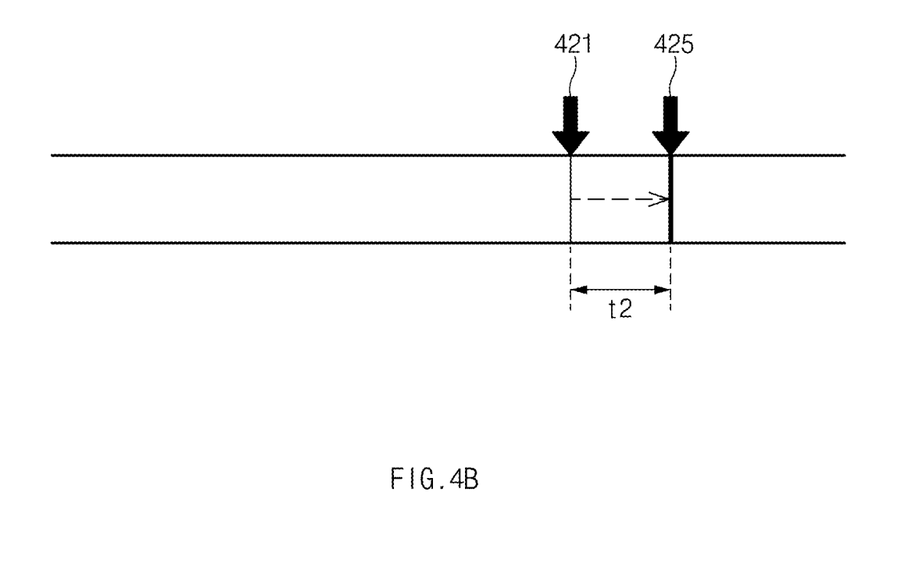

FIGS. 4A and 4B are drawings illustrating an operation of a pulse measurement apparatus according to an embodiment of the present disclosure.

FIG. 4A illustrates an operation of measuring a pulse of a user if a frequency band of a filter is set to a first frequency band. FIG. 4B illustrates an operation of measuring a pulse of a user if a frequency band of a filter is set to a second frequency band.

Assuming that a pulse of a regular adult has a value between 50 bpm and 140 bpm, the first frequency band may be defined based on an average value among values between 50 bpm and 140 bpm. Since a deviation of a pulse is large for each user, the first frequency band may be defined as a wide range.

The second frequency band may be defined based on an average pulse of the user, analyzed by learning pulse information detected from the user and analyzing an average pulse. The second frequency band may be defined as a narrower band than the first frequency band.

As shown in FIG. 4A, a pulse measurement apparatus 100 of FIG. 2 may measure a pulse with respect to a reference frequency in the first frequency band if detecting pulse information of the user from a signal of the first frequency band. If reference numeral 411 denotes a reference frequency and if reference numeral 415 denotes a frequency at which a pulse signal of the user is actually detected, a time taken for the pulse measurement apparatus 100 to measure a pulse of the user with respect to the reference frequency 411 may be t1.

As shown in FIG. 4B, the pulse measurement apparatus 100 may measure a pulse with respect to a reference frequency in the second frequency band if detecting pulse information of the user from a signal of the second frequency band.

If reference numeral 421 denotes a reference frequency and if reference numeral 425 denotes a frequency at which a pulse signal of the user is actually detected, a time taken for the pulse measurement apparatus 100 to measure a pulse of the user with respect to the reference frequency 421 may be t2 (where t2<0).

If setting a frequency band of a filter 130 of FIG. 2 to the second frequency band based on learning data of pulse information detected from the user, the pulse measurement apparatus 100 may further reduce a pulse measurement time from t1 to t2.

A description will be given in detail of an operation of the pulse measurement apparatus 100 according to an embodiment of the present disclosure, including the above-mentioned configuration.

Figure 5:
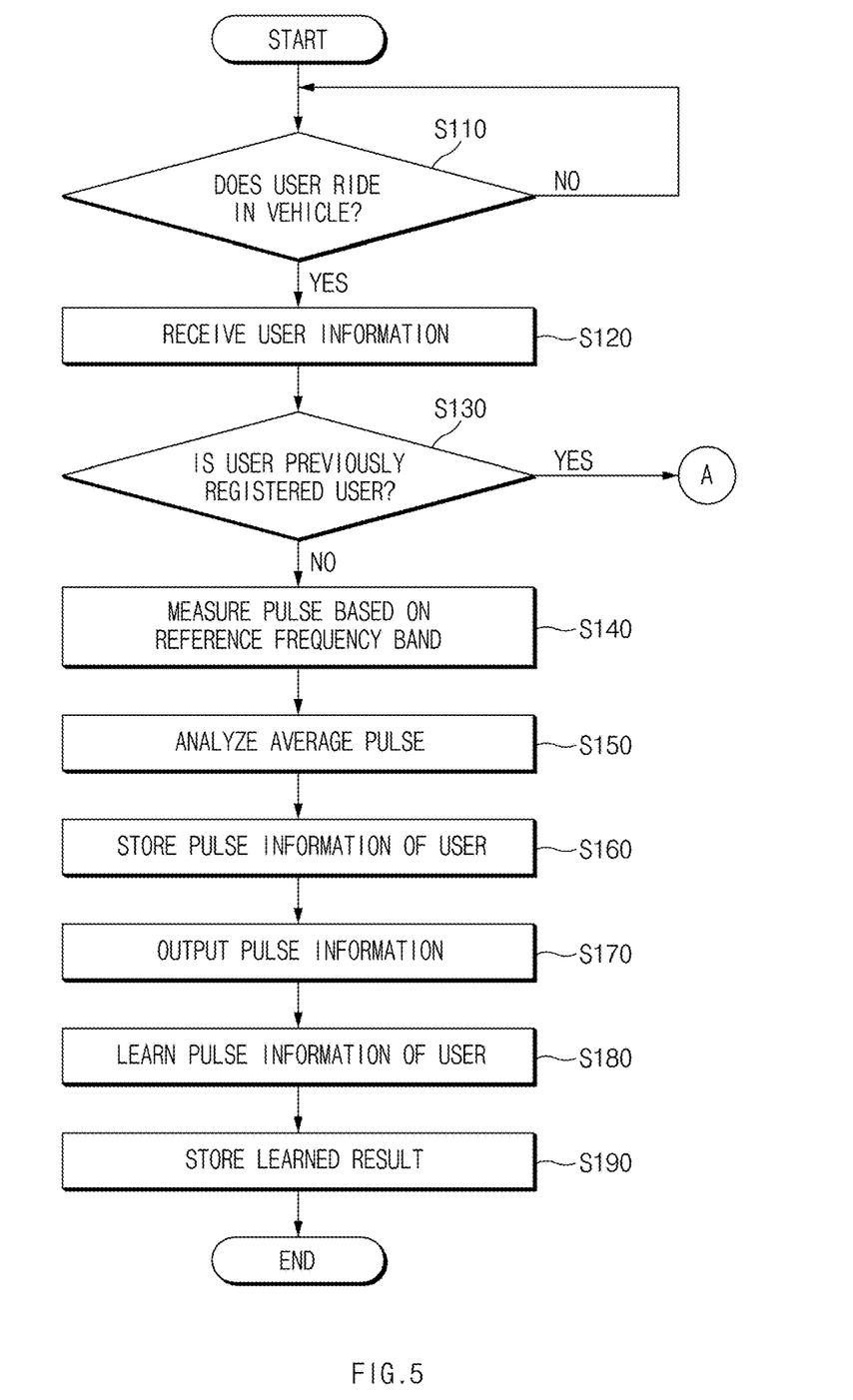
FIGS. 5 and 6 are flowcharts illustrating an operation of a non-contact pulse measurement method according to an embodiment of the present disclosure.
Figure 6:
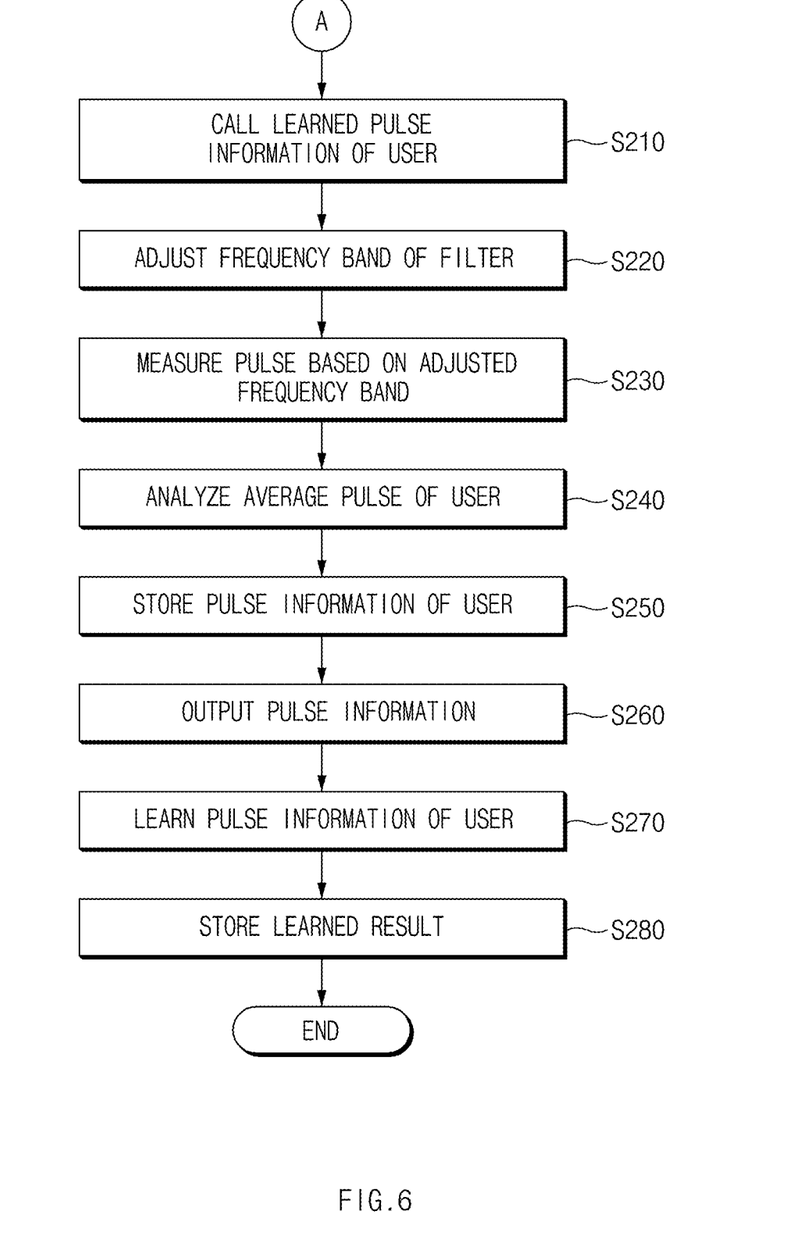

FIGS. 5 and 6 are flowcharts illustrating an operation of a non-contact pulse measurement method according to an embodiment of the present disclosure.

FIG. 5 illustrates an initial operation of a pulse measurement apparatus.

Referring to FIG. 5, a pulse measurement apparatus 100 of FIG. 1 may receive user information from a vehicle device 10 of FIG. 1 in operation S120 if a user rides in a vehicle in operation S110. In operation S130, the pulse measurement apparatus 100 may recognize a user based on the user information received in operation S120 and may determine whether the recognized user is a previously registered user.

If the recognized user is not the previously registered user in operation S130, the pulse measurement apparatus 100 may measure a pulse of the recognized user based on a reference frequency band (a first frequency band) in operation S140.

In operation S140, the pulse measurement apparatus 100 may transmit a first signal to the user during a predetermined time and may measure a pulse of the recognized user from a signal of the reference frequency band in a second signal reflected from the user.

In operation S150, the pulse measurement apparatus 100 may analyze an average pulse based on the result of measuring the pulse in operation S140. In operation S160, the pulse measurement apparatus 100 may detect pulse information of the user based on the result of analyzing the average pulse in operation S150 and may store the detected pulse information in a storage 140 of FIG. 2.

In operation S170, the pulse measurement apparatus 100 may output the pulse information of the user detected in operation S160.

If the pulse measurement of the user is completed, the pulse measurement apparatus 100, in operation S180, may learn the pulse information of the user, stored in operation S160. In operation S190, the pulse measurement apparatus 100 may store the learned result in the storage 140. The learned result stored in operation S190 may be used to adjust a frequency band of the filter 130 when a pulse of the user is measured later.

If the recognized user is the previously registered user in operation S130, the pulse measurement apparatus 100 may perform an operation from 'A' of FIG. 6.

Referring to FIG. 6, the pulse measurement apparatus 100 may call learned pulse information of the previously registered user and may determine a frequency band of a filter 130 of FIG. 2 in operation S210. In operation S220, the pulse measurement apparatus 100 may adjust a frequency band of the filter 130 based on information of the determined frequency band.

In operation S230, the pulse measurement apparatus 100 may measure a pulse of the user based on the frequency band (a second frequency band) adjusted in operation S220.

In operation S230, the pulse measurement apparatus 100 may transmit a first signal to the user during a predetermined time and may measure a pulse of the user from a signal of an adjusted frequency band in a second signal reflected from the user.

In operation S240, the pulse measurement apparatus 100 may analyze an average pulse based on the result of measuring the pulse in operation S230. In operation S250, the pulse measurement apparatus 100 may detect pulse information of the user based on the result of analyzing the average pulse in operation S240 and may store the detected pulse information in the storage 140 of FIG. 2.

In operation S260, the pulse measurement apparatus 100 may output the pulse information of the user, detected in operation S250.

In operation S270, the pulse measurement apparatus 100 may learn the pulse information of the user, which is stored in operation S260, and pulse information previously learned for the user if the pulse measurement of the user is completed. In operation S280, the pulse measurement apparatus 100 may store the learned result in the storage 140 of FIG. 2.

Figure 7:
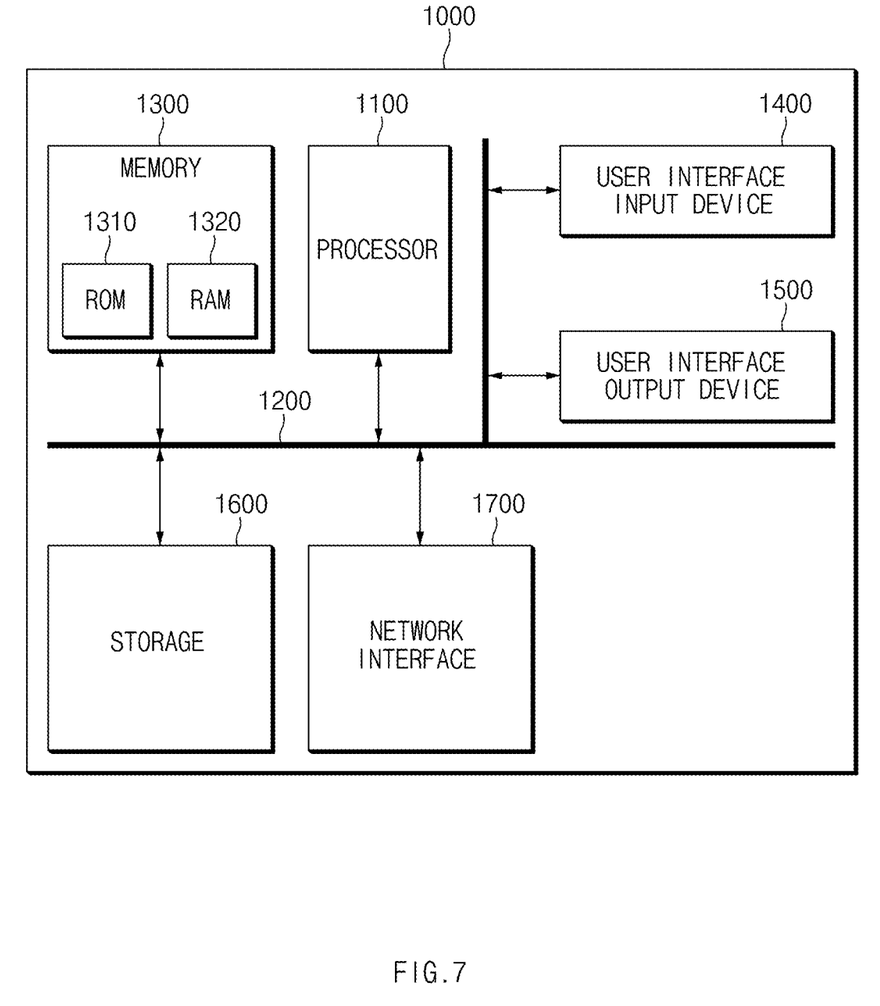
FIG. 7 is a block diagram illustrating a configuration of a computing system in which a method according to an embodiment of the present disclosure is executed.

FIG. 7 is a block diagram illustrating a configuration of a computing system in which a method according to an embodiment of the present disclosure is executed.

Referring to FIG. 7, a computing system 1000 may include at least one processor 1100, a memory 1300, a user interface input device 1400, a user interface output device 1500, a storage 1600, and a network interface 1700, which are connected with each other via a bus 1200.

The processor 1100 may be a central processing unit (CPU) or a semiconductor device for processing instructions stored in the memory 1300 and/or the storage 1600. Each of the memory 1300 and the storage 1600 may include various types of volatile or non-volatile storage media. For example, the memory 1300 may include a read only memory (ROM) 1310 and a random-access memory (RAM) 1320.

The operations of the methods or algorithms described in connection with the embodiments disclosed in the specification may be directly implemented with a hardware module, a software module, or combinations thereof, executed by the processor 1100. The software module may reside on a storage medium (e.g., the memory 1300 and/or the storage 1600) such as a RAM, a flash memory, a ROM, an erasable and programmable ROM (EPROM), an electrically EPROM (EEPROM), a register, a hard disc, a removable disc, or a compact disc-ROM (CD-ROM). A storage medium may be coupled to the processor 1100. The processor 1100 may read out information from the storage medium and may write information in the storage medium. Alternatively, the storage medium may be integrated with the processor 1100. The processor and the storage medium may reside in an application specific integrated circuit (ASIC). The ASIC may reside in a user terminal. Alternatively, the processor and storage medium may reside as a separate component of the user terminal.

According to an embodiment of the present disclosure, the pulse measurement apparatus may reduce a pulse measurement time by setting a filtering frequency band of a received signal using learning data for pulse information of the user when measuring a pulse of the user in a non-contact manner.

While the present disclosure has been described with reference to the embodiments herein, it will be apparent to those skilled in the art that various changes and modifications may be made without departing from the spirit and scope of the present disclosure.

Therefore, embodiments of the present disclosure are not limiting, but illustrative, and the spirit and scope of the present disclosure is not limited thereto. The spirit and scope of the present disclosure should be interpreted by the following claims, it should be interpreted that all technical ideas that are equivalent to the present disclosure are included in the spirit and scope of the present disclosure.

What is claimed is:
1. A vehicle system comprising:
at least one vehicle device configured to recognize a user who rides in a vehicle and to provide information of the user; and
a pulse measurement apparatus configured to recognize the user based on the information of the user received from the at least one vehicle device, to set a frequency band of a filter to a first frequency band or a second frequency band based on information of the user, and to detect pulse information of the user based on an extracted signal that is extracted from a reflected signal that is reflected from the user by the filter when measuring a pulse of the user.

2. The vehicle system of claim 1, wherein the pulse measurement apparatus is configured to set the frequency band of the filter to the first frequency band when the user is not a previously registered user and to set the frequency band of the filter to the second frequency band based on learning data stored in response to the user when the user is the previously registered user, wherein the previously registered user is registered based on information input by the user or based on user information received from a vehicle device, and wherein registration information of the previously registered user is stored in a storage.

3. The vehicle system of claim 1, wherein the pulse measurement apparatus is configured to output the detected pulse information of the user to at least one of a control system or a display device in the vehicle.

4. The vehicle system of claim 1, wherein the at least one vehicle device includes at least one of a smart key control device, a vehicle communication device, and a seat control device.

5. The vehicle system of claim 1, wherein the pulse measurement apparatus is configured to be installed in a seat of the vehicle and measure a pulse of a user who sits on the seat by a radio wave signal.

6. The vehicle system of claim 1, further comprising:
a communicator configured to transmit a transmitted signal to the user and receive the reflected signal that is reflected from the user during a predetermined time.

7. The vehicle system of claim 1, further comprising:
a setting device configured to set the frequency band of the filter to the first frequency band or the second frequency band.

8. The vehicle system of claim 1, further comprising:
a pulse detector configured to measure the pulse from the extracted signal that is extracted by the filter, to analyze an average pulse, and to detect pulse information of the user from the analyzed average pulse.

9. The vehicle system of claim 1, further comprising:
a learning device configured to learn the detected pulse information of the user and generate learning data based on the learned detected pulse information.

10. The vehicle system of claim 9, wherein the learning device is configured to store the generated learning data.

11. The vehicle system of claim 9, further comprising:
a storage configured to register information of the user when the user is not a previously stored user and to store the detected pulse information of the user in response to the registered information of the user.

12. The vehicle system of claim 1, further comprising:
a storage configured to register information of the user and to store the detected pulse information of the user in response to registering the information of the user.

* * * * *